(12) United States Patent
Blew et al.

(10) Patent No.: US 6,711,948 B2
(45) Date of Patent: Mar. 30, 2004

(54) METHOD AND APPARATUS FOR TESTING OF SHEET MATERIAL

(75) Inventors: Austin R. Blew, Lehighton, PA (US); Alexander Eidukonis, Stroudsburg, PA (US)

(73) Assignee: Lehighton Electronics Inc., Lehighton, PA (US)

( * ) Notice: Subject to any disclaimer, the term of this patent is extended or adjusted under 35 U.S.C. 154(b) by 0 days.

(21) Appl. No.: 10/234,747

(22) Filed: Sep. 3, 2002

(65) Prior Publication Data

US 2003/0000301 A1 Jan. 2, 2003

Related U.S. Application Data

(63) Continuation of application No. 09/812,741, filed on Mar. 20, 2001, now Pat. No. 6,443,002, which is a continuation of application No. 09/316,677, filed on May 21, 1999, now Pat. No. 6,202,482, which is a continuation-in-part of application No. 09/274,487, filed on Mar. 23, 1999, now Pat. No. 6,205,852.

(60) Provisional application No. 60/079,058, filed on Mar. 23, 1998.

(51) Int. Cl.[7] .................................................. G01L 5/04

(52) U.S. Cl. ......................................................... 73/159

(58) Field of Search ............................ 73/159, 160, 856

(56) References Cited

U.S. PATENT DOCUMENTS

| 4,865,677 | A | * | 9/1989 | Matsushita et al. | .......... 156/353 |
| 4,875,092 | A | * | 10/1989 | Yamanishi et al. | .......... 358/526 |
| 4,893,322 | A | * | 1/1990 | Hellmick et al. | ............ 378/173 |
| 4,914,452 | A | * | 4/1990 | Fukawa | ...................... 347/214 |
| 6,280,103 | B1 | * | 8/2001 | Zawodny et al. | ............ 396/515 |
| 6,452,660 | B1 | * | 9/2002 | Nguyen-Nhu | ................. 352/72 |

* cited by examiner

*Primary Examiner*—Max Noori
(74) *Attorney, Agent, or Firm*—Duane Morris LLP

(57) ABSTRACT

An apparatus for testing of electrical, mechanical, physical and/or chemical properties of material in sheet form includes a cassette for holding of sheets and sensors rigidly mounted relative to the cassette. The sensors may be mounted adjacent a test location exterior to the cassette. The cassette and the sensors may be so configured and positioned that a suitable end effector may move sheets of material between storage locations in the cassette and test locations adjacent the sensors. A method for testing sheet material includes the steps of placing the sheet material in a cassette, and conducting tests employing one or more sensors rigidly mounted with respect to the cassette. The method may include employing an end effector to remove the sheet from the cassette, to position the sheet stepwise in several positions relative to the sensors, and to replace the sheet in the cassette upon completion of testing. Materials to be tested include flat panels for computer screens and other applications and semiconductor wafers.

18 Claims, 9 Drawing Sheets

METHOD AND APPARATUS FOR TESTING OF SHEET MATERIAL

RELATED APPLICATIONS

This application is a continuation of copending U.S. patent application No. 09/812,741, filed Mar. 20, 2001, now U.S. Pat. No. 6,443,002, which is a continuation of U.S. patent application No. 09/316,677, filed May 21, 1999, now U.S. Pat. No. 6,202,482, which is a continuation-in-part of U.S. patent application No. 09/274,487, filed Mar. 23, 1999, now U.S. Pat. No. 6,205,852, which claims priority from U.S. Provisional Patent Application No. 60/079,058, filed Mar. 23, 1998, which application is incorporated by reference herein.

FIELD OF THE INVENTION

This application relates to the field of testing of sheet materials, and in particular testing of thin glass sheets, such as glass sheets for use in computer flat panel displays, or for semiconductor wafers.

BACKGROUND OF THE INVENTION

Glass sheets or panels are conventionally maintained, after fabrication of the glass sheets, and before assembly into products, such as flat panel displays, in cassettes. Similarly, semiconductor wafers are placed in cassettes. Cassettes are essentially boxes sized to accommodate sheets or cassettes of a selected size. In one existing design of cassettes, there are provided projecting inward from the sides of the cassette panel supports. A defined distance separates the panel supports. The defined distance is selected to permit an end effector of a robot to pass between the panel supports, so as to remove or insert the panel in the cassette.

After fabrication, and after various steps during processing, panels, semiconductor wafers, and other materials in sheet form, are tested for a variety of physical, electrical, mechanical and chemical properties. Typically, upon fabrication, the panels or wafers are placed in the cassette by a robot with an end effector that engages the panel or wafer in such a manner as to minimize damage. When it is desired to test the panel or wafer, an end effector of a robot is inserted into the cassette, engages the panel or wafer, and transports the panel or wafer from the cassette to a testing device. The robot then places the panel or wafer on suitable supports on the testing device. A handler in the testing device moves the panel or wafer relative to test heads that carry out various tests on the panel or wafer. Upon completion of testing, the robot again engages the panel or wafer and removes the panel or wafer from the test equipment and returns it to the cassette.

This presents several difficulties. Testing time includes time to remove the panel from the cassette and transport it to the test device, and the time required to remove the panel from the test device and return it to the cassette. Each time the panel or wafer is engaged or disengaged by handling equipment, such as the robot end effector or the handler of the test device, there is a risk of damage. The time required to position the sample or sheet before measurement or testing and replace the sample after measurement or testing is increased by the need to have several devices successively engage and release the wafer or panel.

OBJECTS AND ADVANTAGES OF THE INVENTION

It is an object of the invention to provide a method and apparatus for testing of physical, chemical, electrical and mechanical properties of material in sheet form, such as panels and wafers, that reduces the process time associated with testing the material.

It is a further object of the invention to provide a method and apparatus for testing of material in sheet form that reduces the risk of damage associated with testing of the material.

It is an advantage of the invention that the foregoing objects are achieved.

Additional objects and advantages of the invention will become evident from a review of the detailed description which follows.

SUMMARY OF THE INVENTION

An apparatus for testing of material in sheet form includes a cassette adapted to store one or more sheets of material and one or more sensors rigidly mounted with respect to the cassette.

The sensors may be mounted adjacent a test location exterior to the cassette. The cassette and the sensors may be so configured and positioned that a suitable end effector may move sheets of material between storage locations in the cassette and test locations adjacent the sensors.

A method for testing sheet material includes the steps of placing the sheet material in a cassette, and conducting tests employing one or more sensors rigidly mounted with respect to the cassette. The method may include employing an end effector to remove the sheet from the cassette, to position the sheet stepwise in several positions relative to the sensors, and to replace the sheet in the cassette upon completion of testing.

An apparatus for testing of material in sheet form includes sensors that can be positioned adjacent to a surface of material in sheet form located in a cassette and supports positioned to reduce sag of the material.

A method for testing sheet material includes the steps of placing the sheet material in a cassette, and testing the sheet material while in the cassette.

A cassette according to the invention includes shelves having defined therein test heads for testing properties of material in sheet form.

DETAILED DESCRIPTION OF THE EMBODIMENTS

Figure 1:
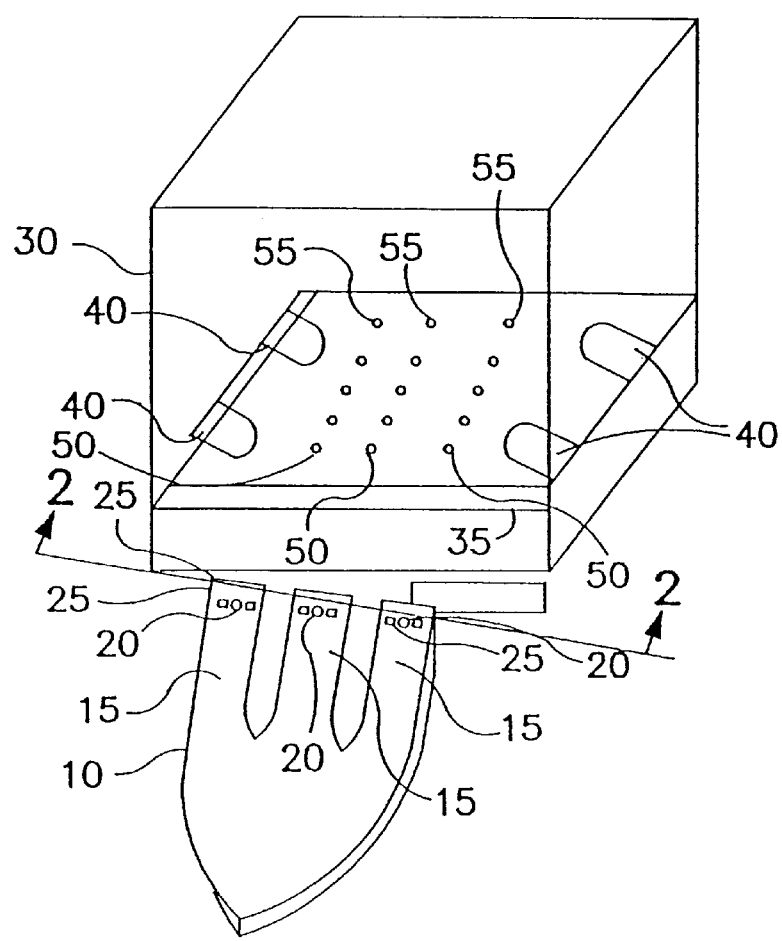
FIG. 1 is a somewhat schematic drawing of an apparatus of the invention positioned relative to an exemplary cassette with an exemplary panel in the cassette.

Referring to FIG. 1, there is shown an apparatus 10 according to the invention. Apparatus 10 is an end effector of a robot arm. More broadly, apparatus 10 is a movable unit. Apparatus 10 is generally a flattened end effector, relatively thin in height compared to length and width. Apparatus 10 is relatively thin in height in this embodiment to permit apparatus 10 to fit beneath a panel or wafer to be tested and over a lower panel or wafer supported in the cassette with adequate clearance. The height of apparatus 10 is dictated principally by the need to clear the next lower panel or wafer in the cassette.

Apparatus 10 has three projecting fingers 15. Each finger 15 has a sensor or test head 20. The number of fingers 15 may be varied as desired depending on the test pattern to be achieved. Each sensor 20 is suitable for positioning adjacent to a panel or wafer positioned in a cassette. Sensor 20 may be any one of numerous types of known compact test heads for testing properties of sheet materials. A wide variety of physical, chemical, mechanical and electrical properties of materials may be tested by use of suitable test heads. For example, the test heads may provide for eddy current sheet resistance testing. Photoreflectance testing may be provided. If photoreflectance testing is provided, then optical fibers are provided to the test heads. Suitable circuitry and wiring are provided in the body of apparatus 10 to permit communication between sensor 20 and controllers and data storage and read out devices. Communication may include control signals sent to sensor 20, and data signals received from sensor 20. Three sensors 20 are shown merely as examples. The number of sensors may be selected as desired, depending on the number of locations to be tested at any one time.

As an alternative, pairs of coplanar sensors and detectors for eddy current detection may be provided in place of each individual sensor 20.

Disposed on opposite sides of sensor 20 are devices 25 for engaging a sheet of material. Devices 25 may be small vacuum heads, or vacuum hold downs, as are well known in the art. Devices 25 serve to prevent relative movement between the panel and sensor 20 while testing is carried out. Air lines (not shown) are provided between vacuum heads 25 and electrically controlled valves (not shown). Device 25 may also support the panel. As there may be sag in the panel, which is otherwise supported only by the panel supports, devices 25 may serve to reduce sag. This may also serve to reduce stresses in the panel that result from sag.

FIG. 1 also shows a cassette 30 having panel or sheet 35 therein. Cassette 30 is generally a box, having a planar horizontal bottom, planar vertical parallel sides, a planar horizontal top, and a planar back wall. A front opening is provided opposite the back wall. The term cassette as used herein includes any container for retaining and protecting multiple sheets of material, such as panels or wafers. Panel supports 40 project inward from the two side walls. FIG. 1 shows only one set of panel supports 40. For convenience of viewing panel supports 40 are shown through panel 35. Cassette 30 has numerous such supports. Numerous panels are supported in a horizontal position in cassette 30.

In a method according to the invention, apparatus 10 is mounted on a robot arm. By robot arm, any device capable of supporting and precisely moving and locating apparatus 10 is meant. Apparatus 10 is positioned relative to a sheet 35 in cassette 30. Initially, apparatus 10 is positioned so that testing may be conducted on sheet 35 at the set of locations closest to the opening of the cassette 30, i.e., at locations 50. Preferably, apparatus 10 is moved into position beneath sheet 35, and then moved upward to contact sheet 35, and then moved upward slightly further a distance sufficient to significantly reduce sag in sheet 35. This last step may involve movement upward of about 5 mils, although the precise distance may vary depending on the distance between sheets and the susceptibility of the particular material and thickness to sag. Apparatus 10 remains with sensors 20 at locations 50, and devices 25 holding sheet 35, to prevent relative movement of sensors 20 to sheet 35. After the test is completed, devices 25 release sheet 35. Apparatus 10 is moved to the next selected set of locations. The process is repeated. Devices 25 engage sheet 35. Sensors 20 carry out testing on sheet 35 at locations 55. Devices 25 disengage sheet 35, and the process is repeated until all desired locations are tested. Of course, the order of testing of various locations on the sheet may be varied. Apparatus 10 must be sufficiently long to permit sensors 20 to contact the desired test location closest to the back wall.

Fingers 15 are shown to provide a certain amount of independent vertical positioning for the three sensors 20. Apparatus 10 may be constructed without fingers, and all sensors 20 supported on a single surface.

The number and relative location of sensors 20 may be selected as desired.

Figure 2:
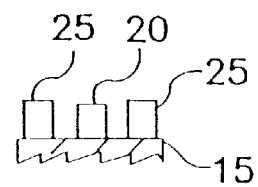
FIG. 2 is a partial sectional view along line 2—2 of an apparatus of FIG. 1.

In summary, in the embodiment of FIGS. 1 and 2, there is provided a robot end effector 10 having one or more sensors 20 or test devices thereon. The end effector 10 is dimensioned to fit between sheets of material 35 in a cassette 30 for holding numerous flat sheets of material. The end effector's length is sufficient to provide testing over all or a substantial portion of a sheet fully inserted in the cassette without moving the sheet. Multiple sensors may be provided on the end effector, and devices may be provided to engage the sheet to prevent relative movement of sensors and sheet during testing. The end effector is dimensioned to fit between panel supports projecting from opposite sidewalls of the cassette.

In a method of the invention in accordance with the foregoing, an end effector with one or more sensors mounted thereon is inserted in a cassette holding sheets of material, and is moved relative to one of the sheets so that the sensor can test the material at selected locations on many points on the surface of the sheet. This process may be repeated for all sheets in the cassette.

Such an effector may be provided, for example, on a Gencobot 7 or 8 GPR robot, available from Genmark.

Figure 3:
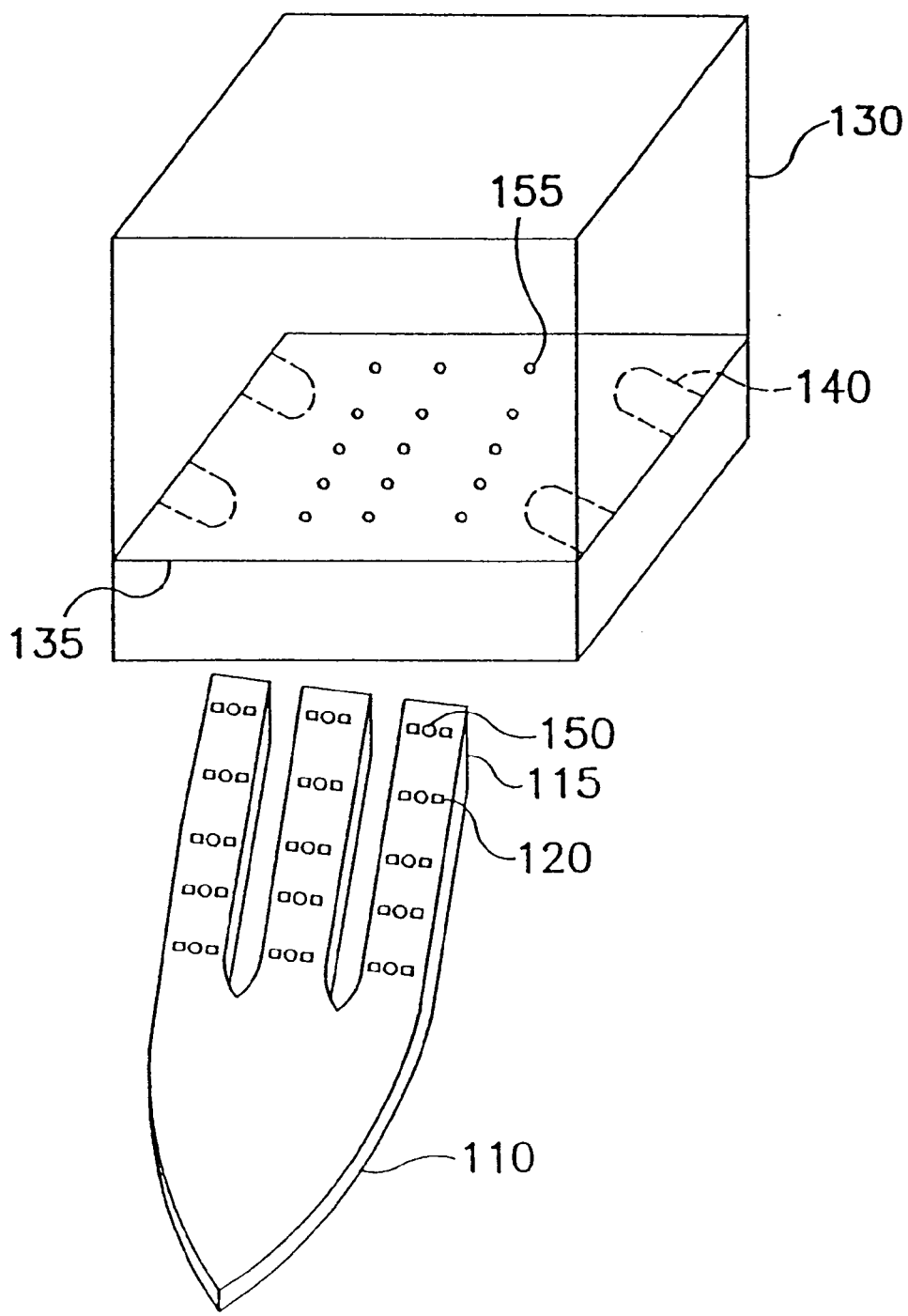
FIG. 3 is a somewhat schematic representation of an alternative embodiment of an apparatus of the invention.
Figure 4:
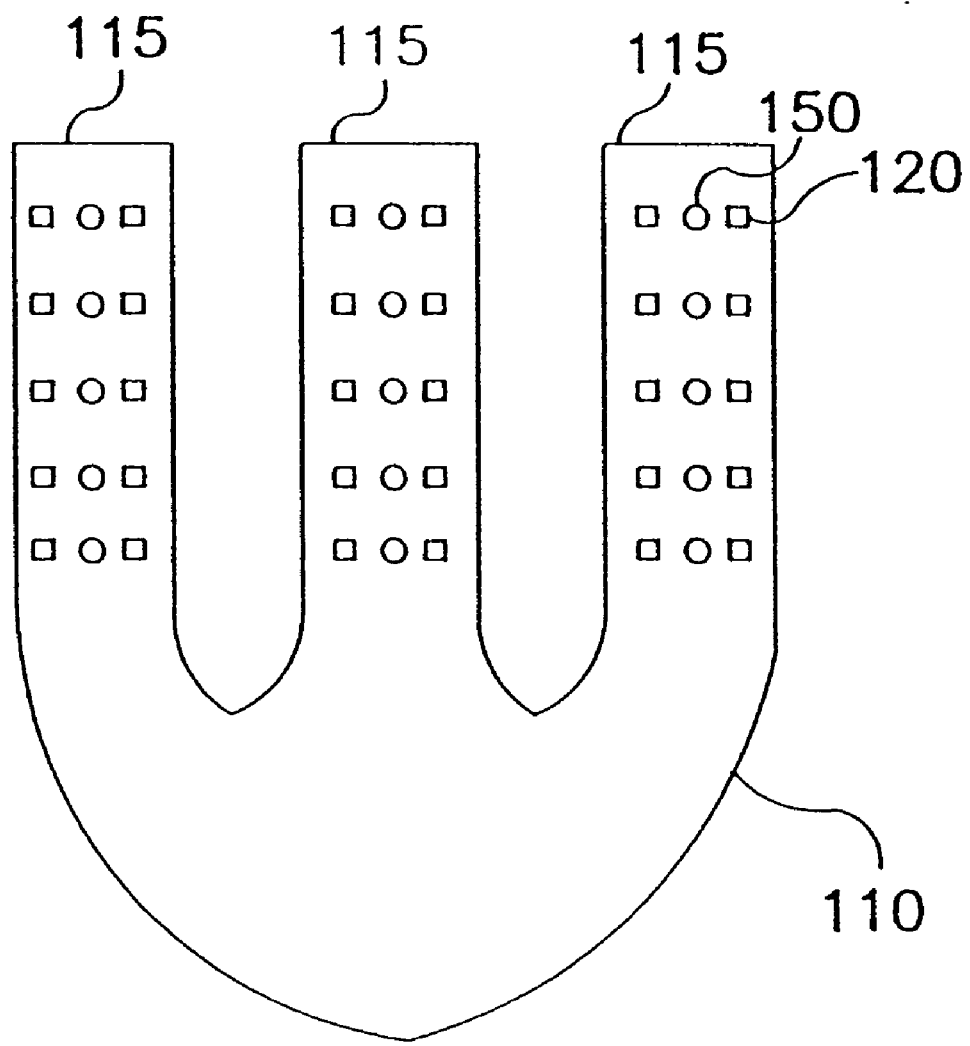
FIG. 4 is a partial plan view of the apparatus of FIG. 3.

Referring now to FIGS. 3 and 4, there is shown an alternative end effector 110 according to the invention. End effector 110 is shown in FIG. 3 in proximity to cassette 130 which has an exemplary flat panel 135 to be tested located therein and supported on supports 140. End effector 110 has an array of sensors 150. Sensors 150 may be any suitable sensor or test head, as discussed above in connection with FIG. 1. Sensors 150 are arranged linearly on each finger 115. Vacuum hold downs 120 are provided adjacent to sensors 150. Sensors are multiplexed to external control electronics and electronics for detecting and storing readings from sensors 150.

In operation, end effector 110 is brought into contact with the sheet material by movement of a robot arm (not shown). End effector 110 is so positioned relative to the sheet material that sensors 150 are positioned adjacent to a substantial portion of the surface of the sheet material. As a result, in a single positioning, sensors 150 may conduct appropriate tests on the sheet material. Preferably, end effector 110 is moved vertically to engage the lower surface of the sheet material and move the sheet material slightly upward to reduce, and preferably to eliminate, sag in the sheet material. For example, end effector 110 may be moved upward about 5 mils after engaging the lower surface of the sheet material. Sag in the sheet material during testing is undesirable as such sag results in anomalous results in various tests. After the vertical movement, the vacuum hold downs 120 are engaged to maintain each sensor 150 stationary relative to the surface of the sheet material. The sensors 150 are then maintained in such proximity to test sites 155 to permit testing. The tests are then carried out. With multiplexing of the sensors, the tests are not necessarily carried out simultaneously, but in series along each finger of end effector 110. Upon completion of the tests, the vacuum is released. End effector 110 is moved vertically downward until it is no longer in contact with the sheet material. End effector 110 is then moved outward from the opening of cassette 130. End effector 110 is then positioned appropriately relative to the next sheet to be tested in cassette 130, and the tests are conducted. The absence of a need for movement of the end effector during testing of a sheet improves throughput and reduces the risk of damage to the surface of the sheet material.

Figure 5:
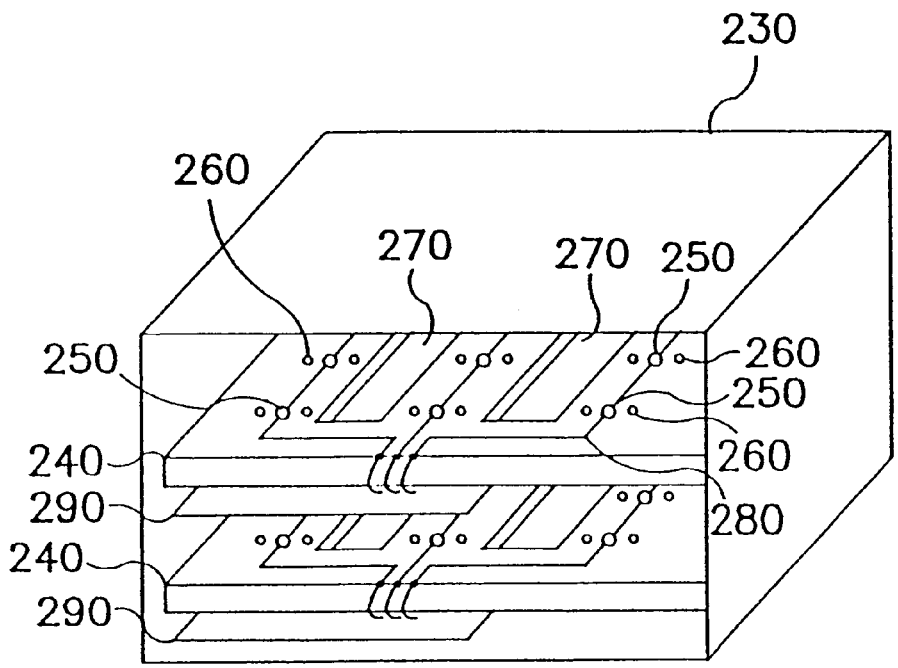
FIG. 5 is a somewhat schematic representation of an alternative embodiment of an apparatus of the invention.
Figure 6:
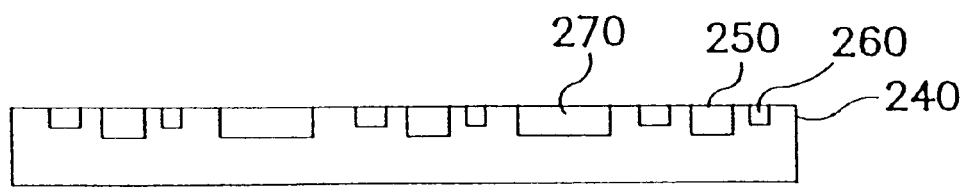
FIG. 6 is a top plan view of a substrate of the invention of FIG. 5.
Figure 7:
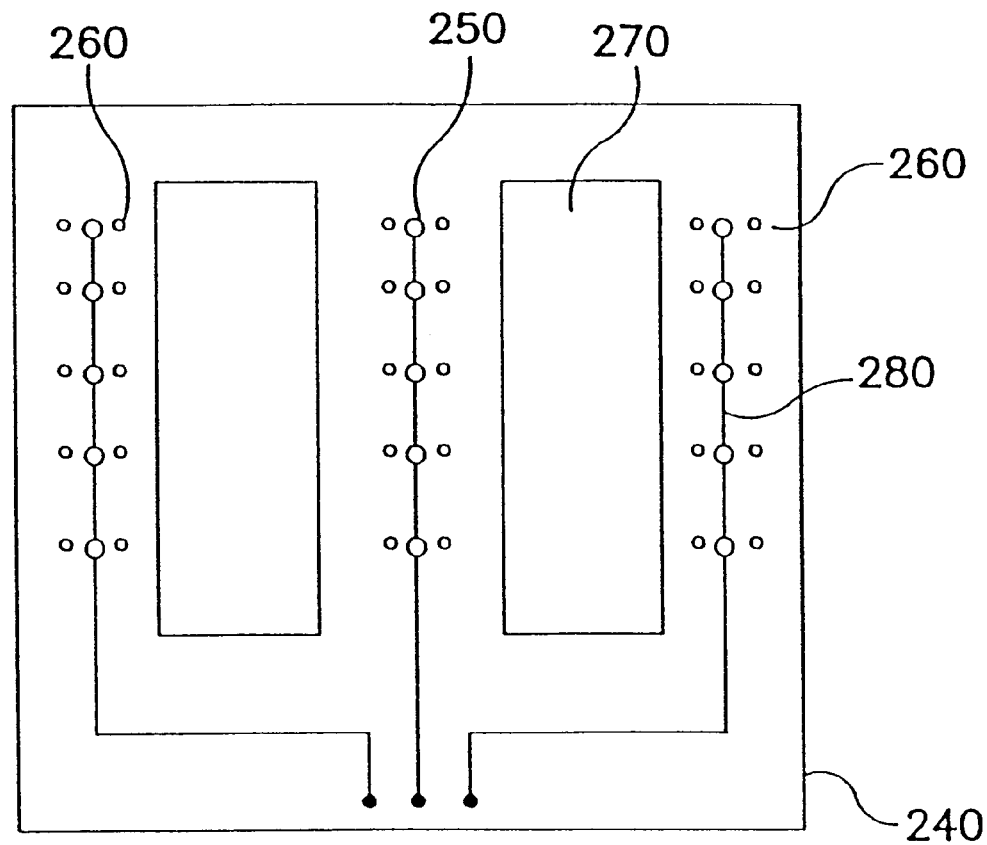
FIG. 7 is a sectional view of the substrate of FIG. 6.

Referring to FIGS. 5, 6 and 7, there is shown an alternative embodiment of an apparatus of the invention for in-cassette testing of sheet material. There is shown a cassette 230 according to the invention. Cassette 230 is essentially a rectangular box with an open front and walls on its other five sides. The walls may be made from conventionally used materials, for cassettes for use in storage of flat panels and wafers, such as metal or ceramics. Cassette 230 has a plurality of sheet shelves 240 for testing of sheet material. Each shelf 240 is a planar sheet of a rigid, non-contaminating material. For example, shelves 240 may be made of one of various ceramics. Shelves 240 may be of metal, such as aluminum; suitable insulation may be provided between the aluminum of the shelf and the conductors. It may be desirable to use heavier conductors than laminated copper for better shielding; if insulated wires are used, the conductive nature of the aluminum is less of a disadvantage. Each shelf 240 is rigidly supported on side walls of cassette 230. Shelves 240 may be bonded to the side walls with an adhesive, be supported on projecting wires attached to the side walls, or otherwise be securely and rigidly supported. Each shelf 240 has a plurality of test heads or sensors 250 formed therein in an array. The array is preferably selected to be of a size relative to the surface of material to be tested to permit conducting of tests on test points including a substantial portion of the surface of the material. Sensors 250 are preferably recessed at the level of the upper, planar surface of shelf 240. Sensors 250 are arranged in several lines, although the patterns of sensor locations may be varied. Vacuum hold downs 260 are provided in pairs adjacent each sensor 250. Vacuum hold downs may be provided in smaller or larger numbers or in different locations as desired. Vacuum hold downs may be in the form of recesses or wells in the body of shelf 240, which wells are in physical communication with a tube. Each shelf 240 preferably has defined therein one or more cutouts or recesses 270 intermediate rows of sensors 250. Recesses 270 are defined to reduce the area of contact between shelf 240 and the sheet material. Recesses 270 also reduce the weight of shelf 240, particularly intermediate the walls of cassette 230. This reduction in weight tends to reduce sag of shelf 240.

Exemplary wiring 280 is shown on the surface of shelf 240. Wiring 280 may be placed on the lower surface of shelf 240, or interior to shelf 240, as desired. In fact, each sensor 250 may have control and readout lines associated therewith. Exemplary circuit boards 290, on which appropriate control and memory electronics may be mounted, are shown immediately below each shelf 240. The appropriate functionality to provide control and memory for test data for the sensors may be physically located elsewhere on the cassette, such as on an outer surface of a cassette wall. Alternatively, wiring 280 of shelves 240 may be electrically connected during testing to electronics mounted externally to cassette 230. Suitable connectors may be provided on each shelf 240 for rapid connection and removal of connecting wiring. By employing externally mounted electronics, additional space is provided within cassette 230. Rather than providing a single board 290 corresponding to each shelf 240, two or more shelves 240 in cassette 230 may be multiplexed to a single board.

As many of the test devices or sensors provide analog data, the boards may include analog-to-digital converters to facilitate the exchange of information with digital devices. Alternatively, the boards may have solely analog electronics. The use of analog devices will reduce the complexity of the boards, although analog-to-digital converters will be required remotely.

If photoreflectance testing is to be provided, in place of wiring to the sensors, optical fibers may be provided. A pair, one for emission of radiation and one for detection of reflected radiation, may be provided at each test head. The optical fibers are preferably placed on the lower surface of the shelf or in cavities defined interior to the shelf. Optical emitters and detectors may be provided on the shelf itself, on an associated board, or remotely.

Vacuum hold downs have tubes or pipes leading thereto from electrically operated valves, which in turn are connected to a pump, vacuum manifold or the like. All hold downs on the surface of a shelf are preferably in physical communication with a single valve, so that all vacuum hold downs on a surface engage and disengage the sheet material simultaneously. The valves may be mounted on the cassette, or may be external. Appropriate couplings are provided for tubes or pipes leading from the vacuum hold downs. Couplings for vacuum lines may be provided to permit quick connection and release.

In an apparatus as shown in FIGS. 5–7, the sheet of material is placed in cassette 230 by a suitable robot end effector. The sheet is placed on the surface of the ceramic shelf 240 to provide contact with the vacuum hold downs 260. If external electronics must be connected with the sheet, the connections are made. The vacuum hold downs 260, as a result of a valve opening in response to a suitable signal from control board or from external electronics, engage the sheet. The test is then carried out During the testing, the test heads 250 are caused to emit suitable signals by control board 290 or external electronics, and to sense resulting fields, in accordance with well-known techniques Upon completion of the testing, any electrical connections can be removed. The sheets remain in the cassette, and the cassette can be transported to the location for the next processing step.

Figure 8:
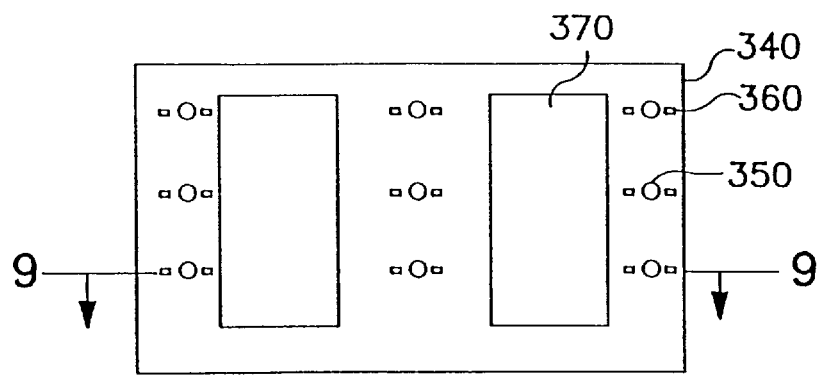
FIG. 8 is a top view of an alternative embodiment of the substrate of FIG. 6.
Figure 9:
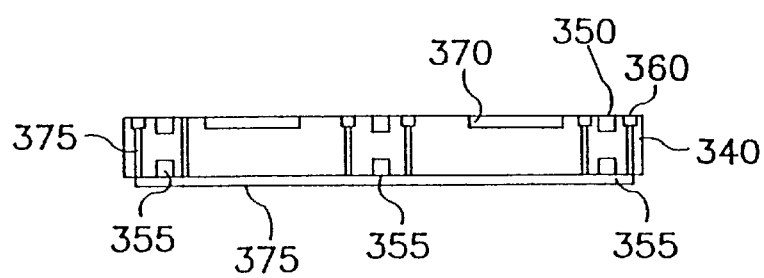
FIG. 9 is a sectional view taken along line 9—9 of FIG. 8.
Figure 10:
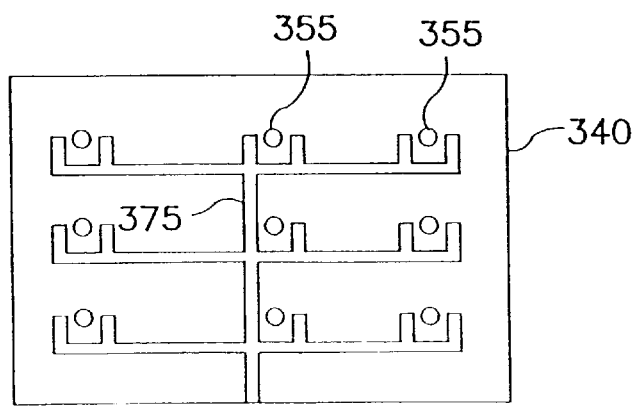
FIG. 10 is a bottom plan view of the substrate of FIG. 8.

Referring now to FIGS. 8 and 9, there is shown an alternative embodiment of the shelf shown in FIGS. 5, 6 and 7. Shelf 340 is configured for conducting tests that require sensor or emitter devices on opposing sides of a panel or wafer. Shelf 340, as with shelf 240, includes sensors or test heads 350, and vacuum hold downs 360 located in recesses in the upper surface of the shelf, and recesses 370. As shown in FIGS. 9 and 10, the lower surface of shelf 340 includes test heads or sensors 355 disposed in recesses formed in the lower surface. Test heads 355 are aligned with test heads 350. Suitably designed test heads 350 on a first shelf and test heads 355 on a second shelf may be inductively coupled through a sheet or wafer to test various properties, in accordance with well-known techniques. Test heads 350 and test heads 355 may be designed in other manners to cooperate to achieve testing of various properties. For example, test head 350 may emit radiation, and test head 355 may detect radiation emitted by test head 350, or radiation emitted by the material as a result of exposure to radiation emitted by test head 350. Existing equipment designs need simply be miniaturized appropriately to fit in the recesses defined in the surface of shelf 340. The design of FIGS. 8–10 may be readily incorporated in a cassette.

Also shown in FIGS. 9 and 10 are lines or tubes 375 running to vacuum devices or hold downs. These lines 375 all physically communicate to a single source. Lines 375 do not block sensors 355. As noted above, a single valve may control communication with a vacuum manifold or pump.

Figure 11:
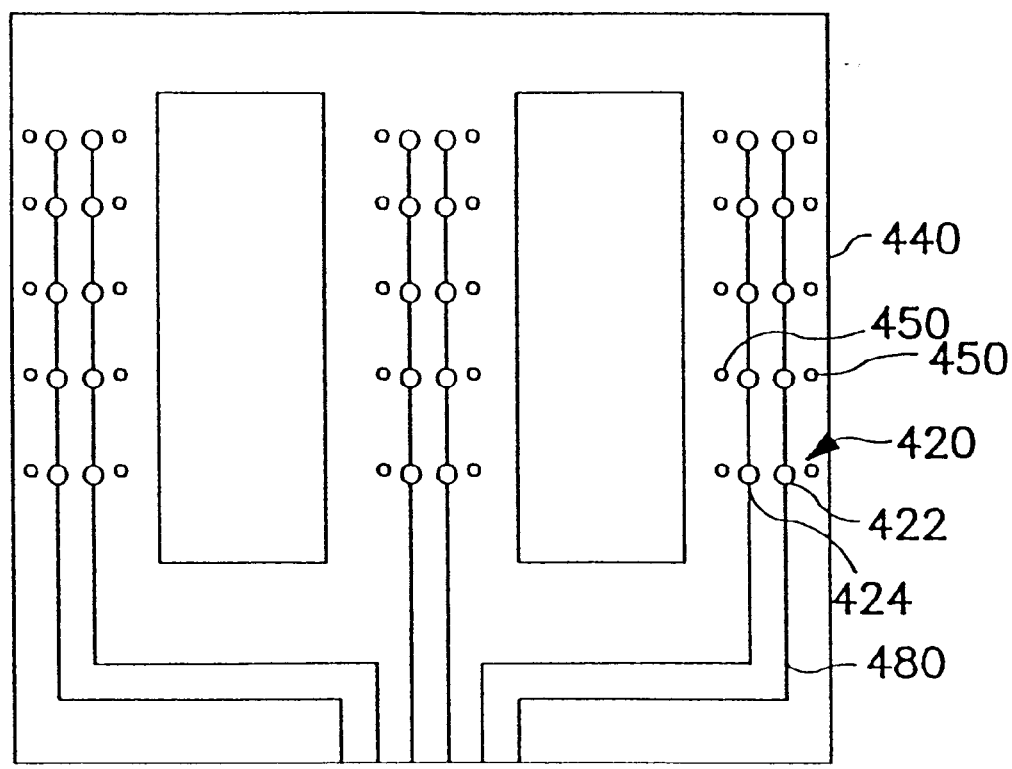
FIG. 11 is a plan view of an alternative design of the upper surface of a substrate of the invention.

Referring now to FIG. 11, there is shown in plan view an alternative embodiment of a shelf according to the invention. In this alternative embodiment, each test point 420 on shelf 440 includes two sensors 422, 424 that are positioned in sufficiently close physical proximity to one another to cooperate in testing materials. For example, both test devices 422, 424 may be coils that may be inductively coupled to each other. Such inductive coupling permits measurement of various properties. Exemplary wiring 480 is shown. Each test point 420 also includes pairs of vacuum hold downs or vacuum devices 450.

Figure 12:
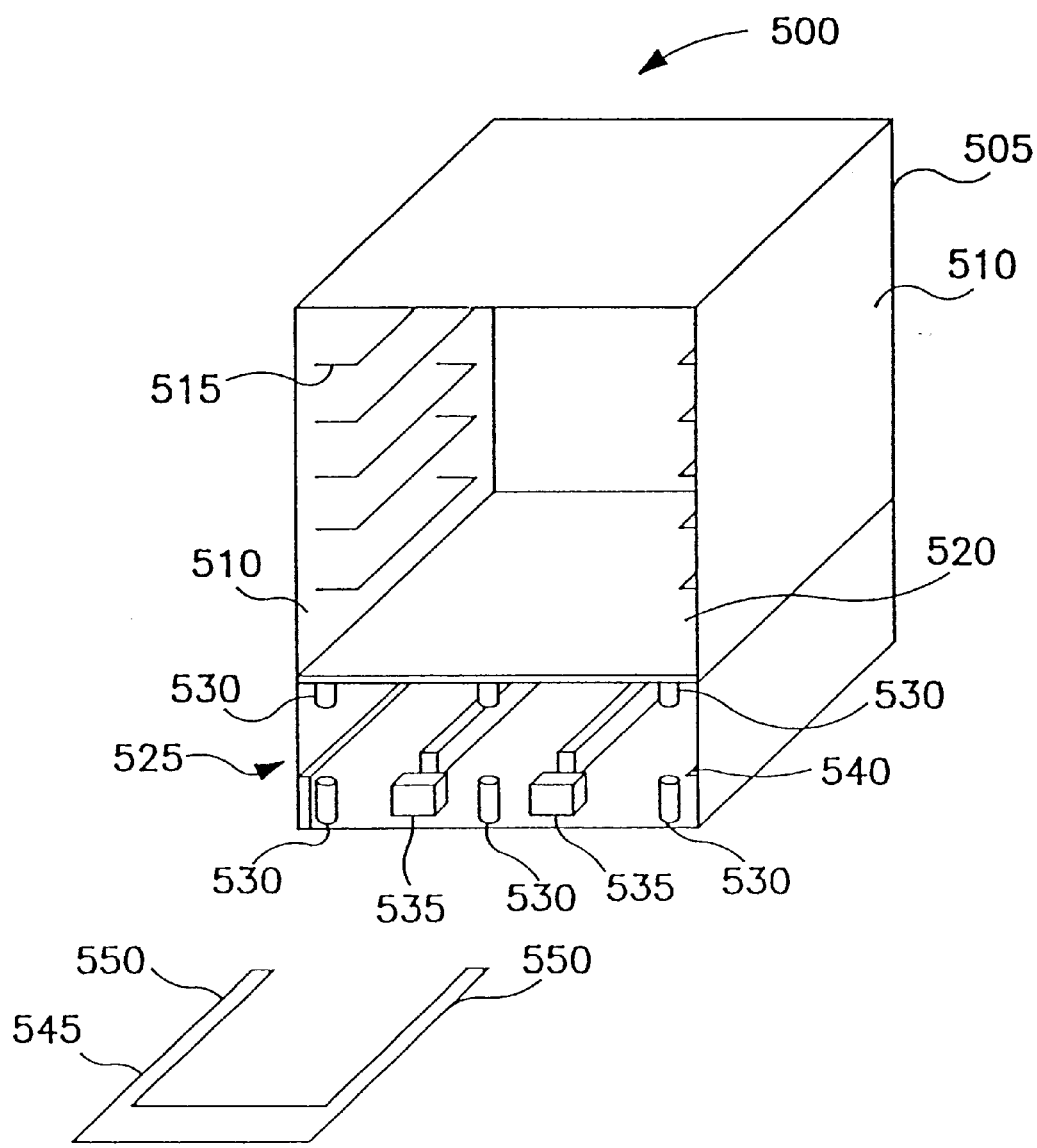
FIG. 12 is a somewhat schematic representation of an alternative embodiment of the invention.

Referring now to FIG. 12, there is shown in a somewhat schematic isometric view a combined cassette and test location unit 500. Cassette 505 is a conventional cassette, in the form of a rectangular box with side walls 510 having sheet supports 515 projecting horizontally inward therefrom. Front opening 520 is defined in cassette 505. Sheet supports 515 are so positioned to permit a suitable end effector to fit between vertically adjacent sheets and between the sheet supports 515. Rigidly attached to the lower wall of cassette 505 is testing location 525. Testing location 525 is also in the form of a rectangular box with a front opening. Testing location 525 includes test heads 530, which are represented schematically. Test heads 530 are preferably contactless sensors for testing physical, mechanical, chemical or electrical properties of sheets placed in test location 525. Such test heads are known in the art. For example, test heads 530 may be sheet resistance sensors, which are positioned in vertically aligned pairs at the front opening of test location 525. Suitable electrical connections to controllers and to data recording software and hardware are provided in accordance with well-known techniques.

Also along the front opening of test location 525, intermediate test heads 530, there are provided vacuum chucks or vacuum hold downs 535. Vacuum chucks 535 are positioned to engage sheets and hold the sheets motionless relative to test heads 530 during each testing step. Vacuum chucks 535 also minimize sag of the sheets during testing. Suitable vacuum lines are provided in accordance with well-known techniques. Inward of front opening of test location 525 there are located substrate supports 540. The substrate supports 540 are elevated to support sheets when those sheets are placed in contact with vacuum chucks 535. The substrate supports 540 are also sufficiently elevated above the floor of test location 525 to provide clearance for a suitable end effector.

Representative end effector 545 is schematically shown adjacent test location 525. End effector 545 has two fingers 550. Fingers 550 are so positioned and dimensioned, and test heads 530, vacuum chucks 535, and substrate supports 540 are all so positioned and dimensioned to permit fingers 550 to position a sheet on substrate supports 540 and vacuum chucks 535 in a position for testing by test heads 530.

In a method of testing sheet materials using unit 500, end effector 545, or another robot end effector, is employed to load sheets into cassette 505. End effector 545 then is inserted into cassette 505, removes a sheet, and moves the sheet into test location 525. When a desired position of the sheet in the horizontal plane relative to test heads 530 is reached, end effector 545 moves downward to cause the sheet to be supported on vacuum chucks 535 and substrate supports 540. If desired, the sheet can be supported on end effector 545 as well. Vacuum chucks 535 then engage the sheet, and testing is carried out by test heads 530. When testing is complete, vacuum chucks 535 disengage the sheet, and end effector 545 engages the sheet again. If measurement at additional locations is desired, end effector 545 moves in a suitable direction until the sheet is positioned properly relative to test heads 530, and the above process is repeated This process is repeated at as many locations as desired. When the testing is complete, end effector 545 removes the sheet from test location 525 and returns the sheet to a storage location in cassette 505. This process may be repeated for each sheet in cassette 505.

The upper set of sensors may be mounted on a vertically movable mount. The mount may be guided on a vertical track. The mount in this configuration is moved vertically by a stepper motor. This configuration is desirable if the amount of sag in the sheet before engagement by the vacuum chuck is greater than the desirable separation between upper and lower sensors. If this configuration is employed, the upper set of sensors is in an upper position when insertion of the sheet by the end effector commences. After insertion of the sheet and engagement by the vacuum chucks, the upper set of sensors is lowered to a lower position. In the lower position, the separation between upper and lower sensors is selected such that any effects of the separation are minimized.

In the embodiment of FIG. 12, it is also possible to mount sensors so that they are movable in a horizontal direction. As it is not necessarily possible to move the sheet laterally within the test area, lateral movement of sensors will permit additional portions of the sheet surface to be tested.

It will be appreciated that the location of the sensors mounted relative to the cassette reduces the distance that sheets must be moved. Also, the use of the end effector, rather than a separate handler, at the test location, reduces the number of pieces of equipment involved and the number of items of equipment that must contact the sheet.

In the embodiment of FIG. 12, rather than a robot end effector, a handler positioned on an elevator may be employed to provide the required vertical and horizontal movement of the sheet into and out of the cassette, between the cassette and the test area, and to various positions within the test area.

Figure 13:
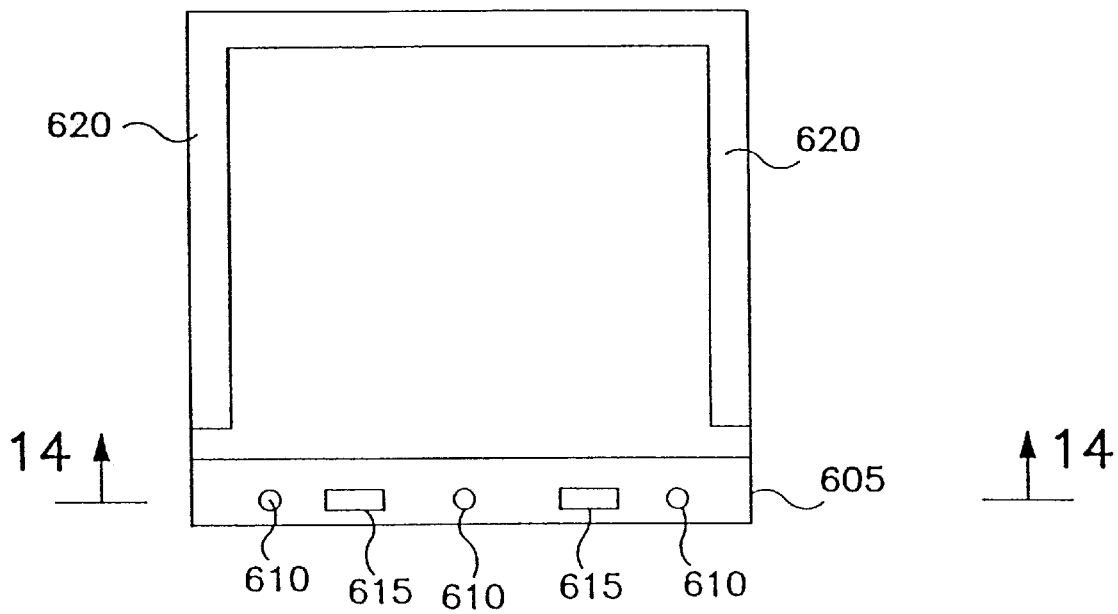
FIG. 13 is a top plan view of an alternative embodiment of a cassette shelf arrangement according to the invention.
Figure 14:
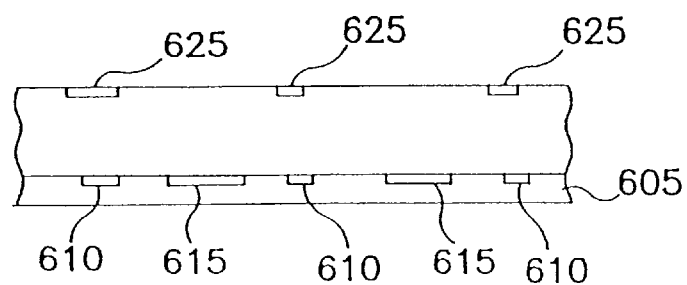
FIG. 14 is a partial front cross-sectional view of the embodiment shown in FIG. 13.

Referring now to FIG. 13, there is provided a top view of an alternative shelf arrangement within a cassette. In this arrangement, there is provided a partial shelf 605 at only the opening of the cassette. The positions of sensors 610 and vacuum hold downs 615 are represented schematically. Suitable electrical connections for sensors 610 and air lines for vacuum hold downs 615 may be provided. Exemplary sheet supports 620 are also shown in the form of ledges protruding inward from the side and rear walls of the cassette. FIG. 14 is a partial front cross-sectional view along line 14—14 of FIG. 13. FIG. 14 shows corresponding upper sensors 625. In this embodiment, an end effector, engaging a sheet, moves the sheet to a desired location relative to sensors 610 and 625. Vacuum hold downs 615 engage the sheet, and appropriate testing is conducted. Vacuum hold downs 615 then release the sheet, and the end effector moves the sheet to a next desired location. The process is repeated until a desired number of measurements have been made. As the sensors and hold downs are located only at the front opening of the cassette in this embodiment, repair and maintenance are simplified. In this embodiment, single sensors may also be employed if desired.

In the embodiments with the sensors in the substrate and in the end effector, either a coil cup, generally of metal foil, such as aluminum, may be used, or individual components may be separately fastened. A coil cup which supports all of the components is useful because it can be constructed so that each sensor may readily be mounted and removed for maintenance.

In any of the embodiments, it will be understood that heads which use microwave radiation to excite the carriers of electric current, induce localized heating, and utilize a thermographic imaging system to measure the physical, chemical, electrical and/or mechanical properties of the sample may be used.

It will be understood that testing is not confined to testing of wafers and panels merely after initial manufacture, but after any suitable stage in the process of manufacture of products incorporating wafers or panels.

It will be appreciated that the foregoing method and apparatus may be used in connection with testing any material in sheet form, and is not limited to use with the items, such as flat panels and semiconductor wafers, named as examples.

While an apparatus and method of the invention have been described with reference to particular embodiments, it will be understood that additional variations are within the scope of the invention.

What is claimed is:

1. Apparatus for testing of material in sheet form, comprising:
   a cassette having a plurality of rigidly supported sheet supports and adapted to store one or more sheets of material on said sheet supports; and
   a plurality of substrate supports for supporting sheet material;
   one or more sensors for testing of properties of material, said one or more sensors being located relative to said substrate supports to be adapted to test sheet material supported on said substrate supports;
   a plurality of vacuum chucks, said vacuum chucks being located relative to said substrate supports to be adapted to engage sheet material supported on said substrate supports;
   said substrate supports, sensors and vacuum chucks being mounted with respect to said cassette.

2. The apparatus of claim 1, wherein said substrate supports, sensors and vacuum chucks are rigidly mounted relative to said cassette.

3. The apparatus of claim 1, wherein said sensors, substrate supports and sensors are so positioned and dimensioned to permit an end effector to position a sheet on said substrate supports and said vacuum chucks in a position for testing by said sensors.

4. The apparatus of claim 1, wherein said sensors comprise sensors for testing electrical properties.

5. The apparatus of claim 4, wherein said sensors comprise sheet resistance sensors.

6. The apparatus of claim 1, wherein said sensors are movable in a horizontal direction.

7. The apparatus of claim 1, wherein said cassette comprises side walls, said sheet supports being rigidly supported on said side walls.

8. A method of testing one or more properties of material in sheet form, comprising the steps of:
   inserting an end effector into a cassette having a plurality of rigidly supported sheet supports;
   removing a sheet of material from the cassette employing said end effector;
   using said end effector to place said sheet of material in a test location, said sheet of material being supported in said test location by a plurality of substrate supports, said substrate supports being rigidly mounted with respect to said cassette;
   employing sensors mounted with respect to said cassette to test said sheet of material in said test location; and
   employing said end effector to return said tested sheet of material to said cassette.

9. The method of claim 8, further comprising the steps of engaging said sheet material in said test material prior to said step of testing, and disengaging the sheet material after said step of testing.

10. The method of claim 9, wherein said steps of engaging and disengaging are carried out by vacuum chucks.

11. The method of claim 10, wherein said vacuum chucks are rigidly mounted with respect to said cassette.

12. The method of claim 8, wherein said sheet of material is a panel for use in a flat panel display.

13. The method of claim 8, further comprising the steps of, after said step of testing, using the end effector to move said sheet of material, placing said material to be supported on said supports, and repeating said step of testing.

14. The method of claim 8, further comprising the steps of, after said step of testing, moving said sensors, and repeating said step of testing.

15. Apparatus for testing of material in sheet form, comprising:
   a cassette, comprising a plurality of rigidly supported sheet supports, side walls and top walls defining a front opening; a plurality of partial shelves located only at said front opening, said partial shelves having an insulating upper surface and sensors mounted on said partial shelves and below said upper surface.

16. The apparatus of claim 15, further comprising vacuum hold downs in said partial shelves.

17. The apparatus of claim 15, wherein said sensors are mounted on upper and lower surfaces of said partial shelves.

18. The apparatus of claim 15, wherein said sensors are adapted to test electrical properties of material.

* * * * *